United States Patent
Eleuteri et al.

(10) Patent No.: US 6,335,439 B1
(45) Date of Patent: *Jan. 1, 2002

(54) METHOD OF PREPARING PHOSPHORAMIDITES

(75) Inventors: Alessandra Eleuteri, Encinitas; Daniel C. Capaldi, San Diego; Vasulinga T. Ravikumar, Carlsbad, all of CA (US)

(73) Assignee: ISIS Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,811

(22) Filed: Jun. 11, 1998

(51) Int. Cl.$^7$ .................................. C07H 1/02; C07H 1/00
(52) U.S. Cl. ........................................ 536/25.34; 536/25.3
(58) Field of Search .................................. 536/25.3, 25.34

(56) References Cited

U.S. PATENT DOCUMENTS

| | | | |
|---|---|---|---|
| 3,687,808 A | 8/1972 | Merigan et al. | 195/28 |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,973,679 A | 11/1990 | Caruthers et al. | 536/27 |
| 4,981,957 A | 1/1991 | Lebleu et al. | 536/27 |
| 5,118,800 A | 6/1992 | Smith et al. | 536/23 |
| 5,132,418 A | 7/1992 | Caruthers et al. | 536/27 |
| RE34,069 E | 9/1992 | Köster et al. | 536/27 |
| 5,212,295 A | 5/1993 | Cook | 536/26.7 |
| 5,319,080 A | 6/1994 | Leumann | 536/27.1 |
| 5,359,044 A | 10/1994 | Cook et al. | 536/23.1 |
| 5,393,878 A | 2/1995 | Leumann | 536/28.2 |
| 5,446,137 A | 8/1995 | Maag et al. | 536/23.1 |
| 5,466,786 A | 11/1995 | Baxter et al. | 514/44 |
| 5,489,677 A | 2/1996 | Sanghvi et al. | 536/22.1 |
| 5,514,785 A | 5/1996 | Van Ness et al. | 536/22.1 |
| 5,519,134 A | 5/1996 | Acevedo et al. | 544/243 |
| 5,567,811 A | 10/1996 | Misiura et al. | 536/25.34 |
| 5,576,427 A | 11/1996 | Cook et al. | 536/23.1 |
| 5,591,722 A | 1/1997 | Montgomery et al. | 514/45 |
| 5,597,909 A | 1/1997 | Urdea et al. | 536/24.3 |
| 5,610,300 A | 3/1997 | Altmann et al. | 544/244 |
| 5,623,070 A | 4/1997 | Cook et al. | 536/27.6 |
| 5,627,053 A | 5/1997 | Usman et al. | 435/91.1 |
| 5,639,873 A | 6/1997 | Barascut et al. | 536/25.3 |
| 5,646,265 A | 7/1997 | McGee | 536/25.34 |
| 5,658,873 A | 8/1997 | Bertsch-Frank et al. | 510/375 |
| 5,670,633 A | 9/1997 | Cook et al. | 536/23.1 |
| 5,700,920 A | 12/1997 | Altmann et al. | 536/221 |
| 5,792,844 A | 8/1998 | Sanghvi et al. | 536/23.1 |

OTHER PUBLICATIONS

Marugg et al. Tetrahedron Letters, 27(20): 2271–2274, 1986.*

Grandas et al. Tetrahedron Letters 30 (5): 543–546, 1989.*

Alul, R.H. et al., "Oxalyl–CPG: a liable support for synthesis of sensitive oligonucleotide derivatives", *Nuc. Acid Res.*, 1991, 19, 1527–1532.

Beaucage, S.L. et al., "The Synthesis of Specific Ribonucleotides and Unrelated Phosphorylated Biomolecules by the Phosphoramidite Method," *Tetrahedron*, 1993, 49(46), 10441–10488.

Beaucage, S.L. et al., "Advances in the Synthesis of Oligonucleotides by the Phosphoramidite Approach", *Tetrahedron*, 1992, 48, 2223–2311.

Beaucage, S.L. et al., "The Functionalization of Oligonucleotides Via Phosphoramidite Derivatives," *Tetrahedron*, 1993, 49(10), 1925–1963.

Bielinska, A. et al., "Regulation of Gene Expression with Double–Stranded Phosphorothioate Oligonucleotides", *Science*, 1990, 250, 997–1000.

Cook, P.D., "Medicinal chemistry of antisense oligonucleotides—future opportunities", *Anti–Cancer Drug Design*, 1991, 6, 585–607.

Dabkowski, W. et al., "Trimethylchlorosilane: a novel activating reagent in nucleotide synthesis via the phosphoramidite route", *J. Chem. Soc. Chem. Commun.*, 1997, 877–878.

De Mesmaeker et al., "Amides as Substitute for the Phosphodiester Linkage in Oligonucleotides", *Synlett.*, 1993, 10, 733–736.

De Mesmaeker et al., "Replacement of the Phosphodiester Linkage in Oligonucleotides: Comparison of two Structural Amide Isomers", *Bioorg. Med. Chem. Lett.*, 1994, 4(7), 873–878.

De Mesmaeker et al., "Comparison of Rigid and Flexible Backbones in Antisense Oligonucleotides", *Bioorg. Med. Chem. Lett.*, 1994, 4(3), 395–398.

Delgado, C. et al., "The Uses and Properties of PEG–Linked Proteins", *Crit. Rev. in Therap. Drug Carrier Sys.*, 1992, 9, 249–304.

Englisch, U. et al., "Chemically Modified Oligonucleotides as Probes and Inhibitors", *Angew. Chem. Int. Ed. Eng.*, 1991, 30, 613–629.

(List continued on next page.)

Primary Examiner—Gary Geist
Assistant Examiner—Howard V. Owens
(74) Attorney, Agent, or Firm—Woodcock Washburn Kurtz Mackiewicz & Norris

(57) ABSTRACT

Improved methods for preparation of phosphoramidite compounds are disclosed. The phosphoramidites are useful, for example, for the preparation of oligonucleotides by solid state oligonucleotide synthetic regimes.

36 Claims, No Drawings

OTHER PUBLICATIONS

Grandas, A. et al., "Synthesis of Deoxycytidine Oligomers Containing Phosphorodithioate Linkages", *Tetra. Lett.*, 1989, 30(5), 543–546.

Greene and Wuts, *Protective Groups in Organic Synthesis*, 2nd Ed., John Wiley & Sons, New York, Chapter 7, 1991.

Hamamoto, S. et al., "New Approach to the Synthesis of Deoxyribonucleoside Phosphoramidite Derivatives", *Chem. Lett.*, 1986, 1401–1404.

Hering, G. et al., "Preparation and Properties of Chloro–N,N–dialkylamino–2,2,2–trichloroethoxy–and Chloro–N,N–dialkylamino–2,2,2–trichloro–1, 1–dimethylethoxyphosphines and their Deoxynucleoside Phosphiteamidates", *Nucleosides & Nucleotides*, 1985, 4(1&2), 169–171.

Kroschwitz, J.I., "Polynucleotides", *Concise Encyclopedia of Polymer Science and Engineering*, 1990, John Wiley & Sons, New York, 858–859.

Lebreton et al., "Antisense Oligonucleotides with Alternating Phosphodiester–"Amides–3" Linkages", *Synlett.*, 1994, 2, 137–140.

Lebreton et al., "Comparison of two Amides as Backbone Replacement of the Phosphodiester Linkage in Oligodeoxynucleotides", *Tetra. Lett.*, 1994, 35(29), 5225–5228.

Martin, P., "Ein neuer Zugang zu 2'–O–Alkylribonucleosiden und Eigenschaften deren Oligonucleotide", *Helvetica Chemica Acta*, 1995, 78, 486–504 (English summary included).

Nasyrov, S. et al., "X–Ray Structure and Absolute Configuration of (–)–Pseudocopsinine ", *J. Chem. Soc. Chem. Commun.*, 1974, 979–980.

Nielsen, J. et al., "Improved synthesis of $(Pr^{i_2}N)_2POCH_2CH_2CN$", *Nucl. Acid Res.*, 1987, 15(8), 3626.

Nielsen, J. et al., "Thermal Instability of Some Alkyl Phosphorodiamidites", *J. Chem. Res.*, 1986, S, 26–27.

Ouchi, T. et al., "Synthesis and Antitumor Activity of Poly(Ethylene Glycol)s Linked to 5'–Fluorouracil via a Urethane of Urea Bond", *Drug Des. & Disc.*, 1992, 9, 93–105.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Secrist, J.A. et al., "Synthesis and Biological Activity of 4'–Thionucleosides", *10th International Rountable: Nucleosides, Nucleotides and their Biological Applications*, Sep. 16–20 1992, Abstract 21, Park City, Utah, 40.

Tanaka, T. et al., "New Approach to the Synthesis of Deoxynucleoside–Phosphoramidite Derivatives", *Tetra. Lett.*, 1986, 27(2), 199–202.

Waldner et al., "Synthesis of Oligodeoxyribonucleotides containing Dimers with Carbamate Moieties as Replacement of the Natural Phosphodiester Linkage", *Bioorg. Med. Chem. Lett.*, 1994, 4(3), 405–408.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

Wu, H. et al., "Inhibition of in vitro transcription by specific double–stranded oligodeoxyribonucleotides", *Gene*, 1990, 89, 203–209.

\* cited by examiner

METHOD OF PREPARING PHOSPHORAMIDITES

FIELD OF THE INVENTION

This invention is directed to methods for the preparation of phosphoramidite compounds that are useful, for example, in the solid phase synthesis of oligonucleotides. The oligonucleotides are useful as diagnostic reagents, research reagents and therapeutics agents.

BACKGROUND OF THE INVENTION

It is well known proteins are significantly involved in many of the bodily states in multicellular organisms, including most disease states. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides, especially oligonucleotides which are complementary to a specific target messenger RNA (mRNA) sequence.

Transcription factors interact with double-stranded DNA during regulation of transcription. Oligonucleotides can serve as competitive inhibitors of transcription factors to modulate the action of transcription factors. Several recent reports describe such interactions (see Bielinska, A., et. al., *Science*, 1990, 250, 997–1000; and Wu, H., et. al., *Gene*, 1990, 89, 203–209).

In addition to functioning as both indirect and direct regulators of proteins, oligonucleotides have also found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides, via Watson-Crick and/or Hoogsteen base pairs, to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in polymerase chain reactions (PCR) has given rise to an expanding commercial industry. PCR has become a mainstay of commercial and research laboratories, and applications of PCR have multiplied. For example, PCR technology is used in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in PCR technology.

Laboratory uses of oligonucleotides are described generally in laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of *Molecular Cloning, A Laboratory Manual*, ibid.) and DNA-Protein Interactions and The Polymerase Chain Reaction (see Vol. 2 of *Current Protocols In Molecular Biology*, ibid).

Oligonucleotides can be custom-synthesized for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, (Tm)); to assist in identification of the oligonucleotide or an oligonucleotide-target complex; to increase cell penetration; to stabilize against nucleases and other enzymes that degrade or interfere with the structure or activity of the oligonucleotides; to provide a mode of disruption (terminating event) once sequence-specifically bound to a target; and to improve the pharmacokinetic properties of the oligonucleotides.

Thus, it is of increasing value to prepare oligonucleotides and other phosphorus-linked oligomers for use in basic research or for diagnostic or therapeutic applications. Consequently, and in view of the considerable expense and time required for synthesis of specific oligonucleotides, there has been a longstanding effort to develop successful methodologies for the preparation of specific oligonucleotides with increased efficiency and product purity.

Synthesis of oligonucleotides can be accomplished using both solution phase and solid phase methods. Oligonucleotide synthesis via solution phase in turn can be accomplished with several coupling mechanisms. However, solution phase chemistry requires purification after each internucleotide coupling, which is labor intensive and time consuming.

The current method of choice for the preparation of naturally occurring oligonucleotides, as well as modified oligonucleotides such as phosphorothioate and phosphorodithioate oligonucleotides, is via solid-phase synthesis wherein an oligonucleotide is prepared on a polymer support (a solid support) such as controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a polystyrene resin available from Perceptive Biosystems. Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. The nucleotide phosphoramidites are reacted with the growing oligonucleotide using "fluidized bed" technology to mix the reagents. The known silica supports suitable for anchoring the oligonucleotide are very fragile and thus cannot be exposed to aggressive mixing.

Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Phosphoramidites typically have been prepared by one of three routes. In the first, a suitably protected nucleobase is reacted with a protected bis-dialkylamino phosphite compound in the presence of 1H-tetrazole or a tetrazole salt. See Nielsen, J. et al., Nucleic Acids Res. 1986, 14, 7391; Nielsen, J. et al., J. Chem. Res.(S) 1986, 26; Hamamoto, S. et al., Chem. Lett. 1986, 1401; and Nielsen, J. et al., Nucleic Acids Res. 1987, 15, 3626. This method is disadvantageous because, inter alia, tetrazole is a health hazard, and poses disposal problems due to its explosive nature.

A second method for the preparation of phosphoramidites involves reacting the 3'-hydroxyl of a nucleoside with a protected dialklyamino chloro phosphitylting reagent. See Hering, G. et al., Nucleosides Nucleotides 1985, 4, 169; and Ugi, I. et al., J. Chem. Soc. Chem. Commun. 1997, 877. This method also is disadvantageous because of the explosive nature of the phosphitylting reagent.

A third method for the synthesis of phosphoramidites involves reacting the 3'-hydroxyl of a nucleoside with a dialklyamino dichloro compound, followed by displacement of chlorine with addition of a protecting group. Tanaka, T. et al., Tetrahedron Lett. 1986, 27, 199.

Phosphordiamidites also can be prepared, for example, by the condensation of a bis(dialkylamino) chlorophosphine with a 5'-protected nucleoside according to the procedure of Grandas et al., *Tetrahedron Letters* 1989 30 (5) 543–546.

Potential applications of oligonucleotides as drugs have created a new challenges in the large-scale synthesis of these compounds. Thus, there remains a need for improved methods of preparing phosphoramidite synthons. The present invention is directed to this, as well as other, important ends.

SUMMARY OF THE INVENTION

The present invention provides novel methods for the preparation of mononucleoside phosphoramidites or oligonucleotide phosphoramidites comprising the steps of:

reacting a mononucleoside or oligonucleotide having a free 3'-hydroxyl with a diaminohalophosphine; and contacting the product of the reaction with a reagent of formula $R_4$—OH, where $R_4$ is a phosphorus protecting group, under conditions of time and temperature sufficient to form the mononucleoside or oligonucleoside phosphoramidite.

In preferred embodiments, methods are provided for the preparation of phosphoramidite compounds of Formula I:

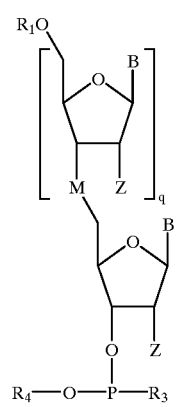

I wherein:

$R_1$ is a hydroxyl protecting group;

B is a nucleobase;

M is an internucleotide linkage;

q is 0 to about 100;

Z is H, OH, F, or a group of formula $R_7$—$(R_8)_n$;

$R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;

$R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

n is from 0 to about 10;

$R_3$ is a group of formula —$N(R_5)(R_6)$;

$R_5$ and $R_6$ are independently alkyl having from one to four carbon atoms, or $R_5$ and $R_6$ taken together with the nitrogen atom to which they are attached form an aliphatic or aromatic five or six membered ring;

$R_4$ is a phosphorus protecting group; comprising:

providing a compound of Formula II:

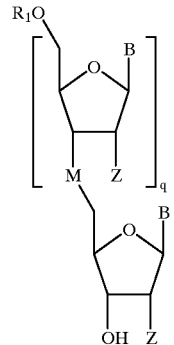

II reacting the compound of Formula II with a diaminohalophosphine of Formula III:

III wherein X is halogen; and $R_2$ is a group of formula —$N(R_5)(R_6)$;
to produce a phosphordiamidite of Formula IV:

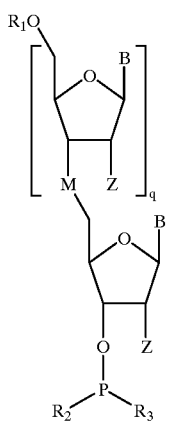

IV and
contacting the phosphordiamidite with a reagent of Formula $R_4$—OH to produce the phosphoramidite of Formula I.

In some preferred embodiments, q is 0.

In some preferred embodiments, $R_1$ is trityl, monomethoxy trityl, dimethoxytrityl, trimethoxytrityl, 2-chlorotrityl, DATE, TBTr, 9-phenylxanthine-9-yl (Pixyl) or 9-(p-methoxyphenyl)xanthine-9-yl (MOX), with trityl, monomethoxy trityl and dimethoxytrityl being more preferred.

In further preferred embodiments, $R_5$ and $R_6$ are each alkyl, with isopropyl being more preferred.

In some preferred embodiments, Z is H, OH, F, or a group of formula $R_7$—$(R_8)_n$ where $R_7$ is $C_1$–$C_{20}$ alkoxy, $C_2$–$C_{20}$ alkenyloxy, or $C_2$–$C_{20}$ alkynyloxy, $R_8$ is hydrogen or O-alkyl, and n is 1.

In further preferred embodiments, $R_4$ is β-cyanoethyl, diphenylsilylethyl, δ-cyanobutenyl, cyano p-xylyl (CPX), N-methyl-N-trifluoroacetyl ethyl (META), acetoxy phenoxy ethyl (APE), or butene-4-yl, with β-cyanoethyl, diphenylsilylethyl, δ-cyanobutenyl or cyano p-xylyl being more preferred.

In some preferred embodiments, X is chlorine.

In further preferred embodiments, each $R_5$ and $R_6$ is alkyl, with isopropyl being preferred.

In more preferred embodiments, $R_4$ is β-cyanoethyl, diphenylsilylethyl, δ-cyanobutenyl acetoxy phenoxy ethyl (APE), or cyano p-xylyl; and each $R_5$ and $R_6$ is alkyl, with isopropyl being preferred.

In further preferred embodiments, the nucleoside is reacted with the diaminohalophosphine in the presence of pyridine, triethylamine or a mixture thereof.

In still further preferred embodiments, the nucleoside phosphordiamidite is contacted with the reagent of formula $R_4$—OH in the presence of triethylamine, pyridine or a mixture thereof.

In even further preferred embodiments, the nucleoside phosphordiamidite is contacted with the reagent of formula $R_4$OH without addition of further reagents.

DESCRIPTION OF PREFERRED EMBODIMENTS

The present invention provides novel methods for the preparation of mononucleoside phosphoramidites or oligo nucleotide phosphoramidites. In some preferred embodiments, the methods of the invention comprise the steps of:

reacting a mononucleoside or oligonucleotide having a free 3'-hydroxyl with a diaminohalophosphine; and contacting the product of the reaction with a reagent of formula $R_4$—OH, where $R_4$ is a phosphorus protecting group, under conditions of time and temperature sufficient to form the mononucleoside or oligonucleoside phosphoramidite.

In more preferred embodiments, methods are provided for the preparation of phosphoramidite compounds of Formula I:

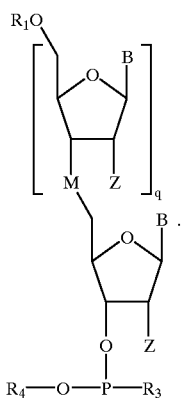

I wherein:

$R_1$ is a hydroxyl protecting group;

B is a nucleobase;

M is an internucleotide linkage;

q is 0 to about 100;

Z is H, OH, F, or a group of formula $R_7$—$(R_8)_n$;

$R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;

$R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides n is from 0 to about 10;

$R_3$ is a group of formula —$N(R_5)(R_6)$;

$R_5$ and $R_6$ are independently alkyl having from one to four carbon atoms, or $R_5$ and $R_6$ taken together with the nitrogen atom to which they are attached form an aliphatic or aromatic five or six membered ring;

$R_4$ is a phosphorus protecting group; comprising:
providing a compound of Formula II:

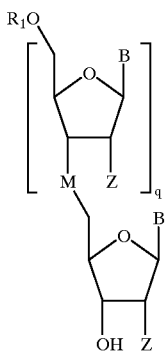

II reacting the compound of Formula II with a diaminohalophosphine of Formula III:

III wherein X is halogen; and $R_2$ is a group of formula —$N(R_5)(R_6)$;
to produce a phosphordiamidite of Formula IV:

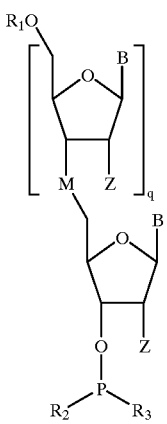

IV and
contacting the phosphordiamidite with a reagent of Formula $R_4$—OH to produce the phosphoramidite of Formula I.

The present invention provides methods for the preparation of phosphoramidite compounds that are comparable in efficiency to the methods currently used for production of phosphoramidites, yet do not require the preparation or use of phosphitylating reagents, such as NC—$CH_2$—$CH_2$—O—P[N(i-pr)$_2$]$_2$, (cyanoethyl-bisdiisopropylamino phosphordiamidite) or the use of tetrazole activators, both of which are potentially explosive. Thus, the methods of the present invention are advantageous in that they afford greater safety than currently used methodologies for phosphoramidite production.

In accordance with the methods of the present invention, a mononucleoside or an oligonucleotide having a free 3'-hydroxyl is reacted with a diaminohalophosphine to produce an intermediate phosphordiamidite, and an amine hydrochloride byproduct. In some especially preferred embodiments of the methods of the invention, the reaction is performed in acetonitrile solvent. Thus, the present invention provides the additional advantage of not requiring the use of halogenated organic solvents, such as dichloromethane, which are disadvantageous because of their toxicity and problems associated with their disposal. It will be appreciated, however, that while use of acetonitrile affords the additional advantages described above, use of halogenated organic solvents, if desired, is also suitable in the methods of the invention.

The mononucleoside or oligonucleotide having a free 3'-hydroxyl is preferably reacted with the diaminohalophosphine in the presence of a base, for example pyridine, triethylamine or a mixture thereof. Hunigs base and diisopropylethylamine are further examples of bases that are amenable to this reaction. A preferred base for this reaction is triethylamine.

In accordance with preferred embodiments of the methods of the invention, the intermediate phosphordiamidite is reacted with an alcohol of formula $R_4$—OH, where $R_4$ is a phosphorus protecting group, to yield the phosphoramidite product. While not wishing to be bound by a specific theory, it is believed that the reaction of the mononucleoside or an oligonucleotide having a free 3'-hydroxyl with a diaminohalophosphine produces an amine hydrochloride byproduct, which serves as an activator in the subsequent reaction between the phosphordiamidite and the alcohol of formula $R_4$—OH.

Preferably, the phosphordiamidite is contacted with the alcohol of formula $R_4$—OH in the same solvent as is used in the reaction between the mononucleoside or oligonucleotide and the diaminohalophosphine, and also in the presence of the same base, for example, pyridine, triethylamine, or a mixture thereof.

As used herein, the term "contacting" means directly or indirectly causing at least two moieties to come into physical association with each other. Contacting thus includes physical acts such as placing the moieties together in a container, or placing together in solution.

In some preferred embodiments, the reaction of the compound of Formula II and the diaminohalophosphine of Formula III, and the contacting of the intermediate phosphordiamidite of Formula IV with the reagent of Formula $R_4$—OH is advantageously performed in "one-pot" i.e., in a single container, thus affording significant benefits of time and expense. The methods of the present invention are therefore especially beneficial in the large-scale production of phosphoramidites. Preferably, the methods of the invention are advantageously performed at ambient pressure and temperature.

The methods of the present invention are useful for the preparation of, inter alia, nucleoside phosphoramidites that can bear protecting groups. Protecting groups are used in the oligonucleotide synthetic methods of the invention for protection of several different types of functionality. In general, protecting groups render chemical functionality inert to specific reaction conditions and can be appended to and removed from such functionality in a molecule without substantially damaging the remainder of the molecule. Representative protecting groups are discussed in Greene and Wuts, *Protective Groups in Organic Synthesis*, Chapter 7, 2d ed, John Wiley & Sons, New York, 1991.

In some preferred embodiments of the invention $R_1$ is a hydroxyl protecting group. A wide variety of hydroxyl protecting groups can be employed in the methods of the invention. Suitable hydroxyl protecting groups include, for example, groups that are useful for protecting 5'-hydroxyl groups during, for example, solid state oligonucleotide synthetic regimes. Preferably, such a 5'-hydroxyl protecting group is stable under basic conditions but can be removed under acidic conditions. Representative hydroxyl protecting groups are disclosed by Beaucage, et al., *Tetrahedron* 1992, 48, 2223–2311, and also in Greene and Wuts, supra, at Chapter 2. Preferred protecting groups used for $R_1$ include trityl, monomethoxy trityl, dimethoxytrityl, trimethoxytrityl, 2-chlorotrityl, DATE, TBTr, 9-phenylxanthine-9-yl (Pixyl) and 9-(p-methoxyphenyl) xanthine-9-yl (MOX).

Removal of hydroxyl protecting groups can be effected by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In preferred embodiments of the methods of the invention, a 5'-protected mononucleoside or oligomeric compound having a free 3'-hydroxyl is reacted with a diaminohalophosphine to produce an intermediate nucleoside phosphordiamidite. The diaminohalophosphine preferably has the formula X—P($R_2$)($R_3$), where X is a halogen, with chlorine being more preferred.

The amino moieties of $R_2$ and $R_3$ can be selected from various amines presently used for phosphoramidites in standard oligonucleotide synthesis. In preferred embodiments of the invention, $R_2$ and $R_3$ each have the Formula —N($R_5$)($R_6$), where $R_5$ and $R_6$ are each independently alkyl having from one to four carbon atoms, or $R_5$ and $R_6$ taken together with the nitrogen atom to which they are attached form an aliphatic or aromatic five or six membered ring. It is generally preferred, but not required, that each $R_5$ and $R_6$ be the same.

In some particularly preferred embodiments of the present invention, $R_5$ and $R_6$ are alkyl, with isopropyl being preferred. Further examples of suitable amines useful as amino moieties of the phosphordiamidites of the invention are described in various United States patents, principally those to M. Caruthers and associates. These include U.S. Pat. Nos. 4,668,777; 4,458,066; 4,415,732; and 4,500,707; the disclosures of which are herein incorporated by reference in their entirety.

The constituent sugars and nucleosidic bases of the phosphoramidites produced by the methods of the present invention can be naturally occurring or non-naturally occurring. Non-naturally occurring sugars and nucleosidic bases are typically structurally distinguishable from, yet functionally interchangeable with, naturally occurring sugars (e.g. ribose and deoxyribose) and nucleosidic bases (e.g., adenine, guanine, cytosine, thymine and uracil). Thus, non-naturally occurring nucleobases and sugars include all such structures which mimic the structure and/or function of naturally occurring species, and which aid in the binding of an oligomer incorporating the nucleobase and/or sugar to a target, or which otherwise advantageously contribute to the properties of such an oligomer.

For example, representative nucleobases suitable for use in the methods of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607, the disclosures of which are herein incorporated by reference in their entirety. The terms "nucleosidic base" and "nucleobase" are further intended to include heterocyclic compounds that can serve as nucleosidic bases, including certain "universal bases" that are not nucleosidic bases in the most classical sense, but function similarly to nucleosidic bases. One representative example of such a universal base is 3-nitropyrrole.

The nucleobases employed in the methods of the present invention can bear protecting groups. Typically, such nucleobase protecting groups are base labile, and serve to protect the exocyclic amino groups of the heterocyclic nucleobases. In some preferred embodiments, this type of protection is achieved by acylation with an acylating reagent such as, for example, benzoylchloride or isobutyrylchloride. These protecting groups are stable to the reaction conditions of the methods of the present invention, as well as the conditions of oligonucleotide synthesis. Typically, such protecting groups are cleaved at approximately equal rates during treatment with base at the end of oligonucleotide synthesis.

The present invention provides methods for the preparation of phosphoramidites having substituents at, for example, the 2'-position. Representative 2'-substituents (i.e., moieties represented by "Z" in the structures herein) include but are not limited to H, OH, F, or a group of formula $R_7$—($R_8$)$_n$ wherein $R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy; and $R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides.

Preferred 2'modifications include 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486) i.e., an alkoxyalkoxy group. A further preferred modification includes 2'-dimethylamino oxyethoxy, i.e., a O($CH_2$)$_2$ON ($CH_3$)$_2$ group, also known as 2'-DMAOE, as described in co-owned U.S. patent application Ser. No. 09/016,520, filed on Jan. 30, 1998, the contents of which are herein incorporated by reference.

Other preferred 2' modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the sugar group, particularly the 3' position of the sugar on the 3' terminal nucleotide or in 2'–5' linked oligonucleotides and the 5' position of 5' terminal nucleotide. The nucleosides of the oligonucleotides may also have sugar mimetics such as cyclobutyl moieties in place of the pentofuranosyl sugar.

Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053 5,639,873; 5,646,265; 5,658,873; 5,670,633; and 5,700,920, certain of which are commonly owned with the present application, each of which is herein incorporated by reference, together with allowed U.S. Pat. No. 5,859,221, which is commonly owned with the present application and is herein incorporated by reference.

In some preferred embodiments, the methods of the invention are employed to prepare phosphoramidites having 2'-O substituents that are polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U. S. patent application Ser. No. 08/398,901, filed Mar. 6, 1995, entitled Oligomeric Compounds having Pyrimidine Nucleotide(s) with 2' and 5' Substitutions, the disclosure of which is hereby incorporated by reference.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992.

The phosphorus protecting group $R_4$, is a group that is useful for protecting phosphorus containing internucleoside linkages during, for example, solid state oligonucleotide synthetic regimes. Examples of such phosphorus protecting groups include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., *Tetrahedron*, 49 No. 10, pp. 1925–1963 (1993); Beaucage, S. L. and Iyer, R. P., *Tetrahedron*, 49 No. 46, pp. 10441–10488 (1993); Beaucage, S. L. and Iyer, R. P., *Tetrahedron*, 48 No. 12, pp. 2223–2311 (1992). See also U.S. Patents Nos.

In some preferred embodiments of the methods of the present invention, mononucleoside phosphoramidite compounds are prepared from nucleosides having a free 3'-hydroxyl. Such mononucleoside phosphoramidites are useful for example, in the solid state synthesis of oligonucleotides. Additionally, the methods of the present invention can be used to prepare dimeric, trimeric, or higher order nucleotide 3'-phosphoramidite compounds, from suitably protected oligomeric compounds having a free terminal 3'-hydroxyl group. Such phosphoramidites are useful, for example, in synthetic regimes wherein an oligomeric "block" is added to a growing chain in a single coupling step. Thus, in preferred embodiments, the compounds of Formula II include both mononucleosides (i.e., q is 0) and oligomers that have a free 3'-hydroxyl (i.e., q is greater than 1). Preferably, q is from 0 to about 100; more preferably from 0 to about 25, even more preferably from about 0 to about 10, with 0 to about 5 being more preferred. In especially preferred embodiments, q is 0, 1 or 2, with 0 being most preferred.

The methods of the present invention can be used to prepare oligomeric 3'-phosphoramidites having a wide variety of internucleotide linkages, represented by "M" in the structures provided herein. Examples of internucleoside linkages which can be present in the compounds of Formula I, II and IV include phosphodiester, phosphorothioate, phosphorodithioate, and phosphonate linkages. Further representative internucleotide linkages include amide or substituted amide linkages, such as those described in Waldner et al., *Synlett*. 1, 57–61 (1994), De Mesmaeker et al., *Synlett*. 10, 733–736 (1993), Lebreton et al., *Synlett*. 2, 137–140 (1994), De Mesmaeker et al., *Bioorg. Medic. Chem. Lett.* 4, 395–398 (1994), De Mesmaeker et al., *Bioorg. Medic. Chem. Lett.* 4, 873–878 (1994), Lebreton et al., *Tet. Letters* 34, 6383–6386 (1993), Lebreton et al., *Tet. Letters* 35, 5225–5228 (1994), Waldner et al., *Bioorg. Medic. Chem. Lett.* 4, 405–408 (1994), and linkages described in U.S. Pat. No. 5,489,677, U.S. Pat. No. 5,792,844, U.S. Pat. No. 5,623,070.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

The term "alkenyl" includes but is not limited to straight chain, branch chain, and alicyclic hydrocarbon groups that have at least one carbon-carbon double bond.

The term "alkynyl" includes but is not limited to straight chain, branch chain, and alicyclic hydrocarbon groups that have at least one carbon-carbon triple bond.

The terms "alkoxy" "alkenyloxy" and "alkynyloxy" denote groups of the formula A-O— where A is, respectively, an alkyl group, and alkenyl group, or an alkynyl group.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, and pyrenyl groups.

The term "heterocycle" denotes an aliphatic or aromatic ring or ring system having at least one heteroatom therein. The term heteroatom means a non-carbon atom, such as O, N or S.

As used herein, the term O-alkylamino denotes a group of formula O-alkyl-$NH_2$. The term O-alkylalkoxy denotes a group of formula -O-alkyl-O-alkyl. The term O-alkylaminoalkyl denotes an O-alkylamino group wherein the amino moiety bears one or more additional alkyl groups. The As used herein, the term "heterocycloalkyl", denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

Halogens include F, Cl, Br and I.

Polyamines are groups having the general formula -[A-NH]$_v$—H; —[NH-A]$_v$; -[A-NH-A]$_v$; or —[NH-A-NH]$_t$—H where A is alkyl, alkenyl or alkynyl, v is greater than one, and t is one or greater.

As used herein, the term "nucleoside" denotes a pentofuranosyl sugar which is bound to a nucleosidic base (i.e, a nitrogenous heterocyclic base or "nucleobase").

As used herein, the term "oligonucleotide" denotes a plurality of pentofuranose units which bear nucleobases, linked by an internucleotide linkage. Included within the definition of "oligonucleotide" are naturally occurring oligonucleotides such as ribose and deoxyribose phosphodiesters, and their analogs such as phosphorothioates, phosphorodithioates, and phosphonates.

As used herein, the term "intercalator" means a moiety that in known to intercalate into double stranded DNA. Typically intercalators are planar molecules, for example acridine.

As used herein, the term "reporter molecule" means a molecule that is detectable. Included within the definition of "reporter molecule" are radiolabels (e.g., compounds containing an enriched amount of a radioactivce atom such as $^{14}$C, $^3$H, or $^{31}$p), chromaphores, fluorophores, and enzymes that are detectable via their enzymatic function.

In some preferred embodiments of the invention amino groups are appended to alkyl or other groups, such as, for example, 2'-alkoxy groups (e.g., where R$_7$ is alkoxy and R$_8$ is NH-alkyl). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Additional advantages and novel features of this invention will become apparent to those skilled in the art upon examination of the examples thereof provided below, which should not be construed as limiting the appended claims.

EXAMPLES

Example 1

5'-O-Dimethoxytritylthymidine-3'-O-(4-cyanomethylbenzyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. 5'-O-DMT thymidine (3.7 mmole), pyridine (5.55 mmol) and acetonitrile (95 ml) are added to the flask followed by bis(diisopropylamino) chlorophosphine (4.44 mmol) at room temperature. The reaction mixture was stirred for 20 minutes and a solution of 4-cyanomethylbenzyl alcohol (4.28 mmole) in acetonitrile (5 ml) dried over 4 A molecular sieves was added. The reaction mixture was stirred at room temperature for 1 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 2

5'-O-Dimethoxytrityl-thymidine-3'-O-(2-cyanoethyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. 5'-O-DMT thymidine (3.7 mmole), pyridine (5.55 mmol) and acetonitrile (95 ml) were added to the flask followed by bis(diisopropylamino) chlorophosphine (4.44 mmol) at room temperature. The reaction mixture was stirred, and then a solution of 3-hydroxypropionitrile (4.28 mmol) in acetonitrile (5 ml) dried over 4 A molecular sieves was added. The reaction mixture was stirred at room temperature for 12 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 3

5'-O-Dimethoxytrityl-thymidine-3'-O-(2-diphenylmethylsilylethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. 5'-O-DMT thymidine (3.7 mmole), pyridine (5.55 mmol) and acetonitrile (95 ml) are added to the flask followed by bis(diisopropylamino)chlorophosphine (4.44 mmol) at room temperature. The reaction mixture is stirred for 20 minutes and a solution of 2-diphenylmethylsilyl ethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 4

5'-O-Dimethoxytritylthymidine-3'-O-(N-methyl-N-trifluoroacetylaminoethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. 5'-O-DMT thymidine (3.7 mmole), pyridine (5.55 mmol) and acetonitrile (95 ml) are added to the flask followed by bis(diisopropylamino)chlorophosphine (4.44 mmol) at room temperature. The reaction mixture is stirred for 20 minutes and a solution of N-methyl-N-trifluoroacetylethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 5

N2-Isobutyryl-5'-O-Dimethoxytrityl-2'-deoxyguanosine-3'-O-(4-cyanomethylbenzyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. 5'-O-DMT-2'-deoxyguanosine (3.7 mmole), triethylamine (5.55 mmol) and acetonitrile (95 ml) were added to the flask followed by bis(diisopropylamino)chlorophosphine (4.44 mmol) at room temperature. The reaction mixture was stirred for 20 minutes and a solution of 4-cyanomethylbenzyl alcohol (4.28 mmole) in acetonitrile (5 ml) dried over 4 A molecular sieves was added. The reaction mixture was stirred at room temperature overnight. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 6

N2-Isobutyryl-5'-O-dimethoxytrityl-2'-deoxyguanosine-3'-O-(2-cyanoethyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. N2-Isobutyryl-5'-O-DMT-2'-deoxyguanosine (3.7 mmole), triethylamine (5.55 mmol) and acetonitrile (95 ml) were added to the flask followed by bis(diisopropylamino)chlorophosphine (4.44 mmol) at room temperature. The reaction mixture was stirred, and then a solution of 3-hydroxypropionitrile (4.28 mmol) in acetonitrile (5 ml) dried over 4 A molecular sieves was added. The reaction mixture was stirred at room temperature for 12 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 7

N2-Isobutyryl-5'-O-dimethoxytrityl-2'-deoxyguanosine-3'-O-(2-diphenylmethylsilylethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N2-Isobutyryl-5'-O-DMT-2'-deoxyguanosine (3.7 mmole), triethylamine (5.55 mmol) and acetonitrile (95 ml) are added to the flask followed by bis(diisopropylamino)chlorophosphine (4.44 mmol) at room temperature. The reaction mixture is stirred for 20 minutes and a solution of 2-diphenylmethylsilyl ethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 8

N2-Isobutyryl-5'-O-dimethoxytrityl-2'-deoxyguanosine-3'-O-(N-methyl-N-trifluoroacetylaminoethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N2-Isobutyryl-5'-O-DMT-2'-deoxyguanosine (3.7 mmole), triethylamine (5.55 mmol) and acetonitrile (95 ml) are added to the flask followed by bis(diisopropylamino)chlorophosphine (4.44 mmol) at room temperature. The reaction mixture is stirred for 20 minutes and a solution of N-methyl-N-trifluoroacetylethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 9

N4-Benzoyl-5'-O-dimethoxytrityl-2'-deoxycytidine-3'-O-(4-cyanomethylbenzyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. N4-Benzoyl-5'-O-DMT-2'-deoxycytidine (3.7 mmole), triethylamine (5.55 mmol) and acetonitrile (95 ml) were added to the flask followed by bis(diisopropylamino)chlorophosphine (4.44 mmol) at room temperature. The reaction mixture was stirred for 20 minutes and a solution of 4-cyanomethylbenzyl alcohol (4.28 mmole) in acetonitrile (5 ml) dried over 4 A molecular sieves was added. The reaction mixture was stirred at room temperature overnight. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 10

N4-Benzoyl-5'-O-dimethoxytrityl-2'-deoxycytidine-3'-O-(2-cyanoethyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. N4-Benzoyl-5'-O-DMT-21-deoxycytidine (3.7 mmole), triethylamine (5.55 mmol) and acetonitrile (95 ml) were added to the flask followed by bis(diisopropylamino)chlorophosphine (4.44 mmol) at room temperature. The reaction mixture was stirred, and then a solution of 3-hydroxypropionitrile (4.28 mmol) in acetonitrile (5 ml) dried over 4 A molecular sieves was added. The reaction mixture was stirred at room temperature for 12 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 11

N4-Benzoyl-5'-O-dimethoxytrityl-2'-deoxycytidine-3'-O-(2-diphenylmethylsilylethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N4-Benzoyl-5'-O-DMT-2'-deoxycytidine (3.7 mmole), triethylamine (5.55 mmol) and acetonitrile (95 ml) are added to the flask followed by bis(diisopropylamino) chlorophosphine (4.44 mmol) at room temperature. The reaction mixture is stirred for 20 minutes and a solution of 2-diphenylmethylsilyl ethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 12

N4-Benzoyl-5'-O-dimethoxytrityl-2'-deoxycytidine-3'-O-(N-methyl-N-trifluoroacetylaminoethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N4-Benzoyl-5'-O-DMT-2'-deoxycytidine (3.7 mmole), triethylamine (5.55 mmol) and acetonitrile (95 ml) are added to the flask followed by bis(diisopropylamino) chlorophosphine (4.44 mmol) at room temperature. The reaction mixture is stirred for 20 minutes and a solution of N-methyl-N-trifluoroacetylethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 13

N6-Benzoyl-5'-O-dimethoxytrityl-2'-deoxyadenosine-3'-O-(4-cyanomethylbenzyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. N6-Benzoyl-5'-O-DMT-2'-deoxyadenosine (3.7 mmole), pyridine (5.55 mmol) and acetonitrile (95 ml) were added to the flask followed by bis(diisopropylamino)chlorophosphine (4.44 mmol) at room temperature. The reaction mixture was stirred for 20 minutes and a solution of 4-cyanomethylbenzyl alcohol (4.28 mmole) in acetonitrile (5 ml) dried over 4 A molecular sieves was added. The reaction mixture was stirred at room temperature for 12 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 14

N6-Benzoyl-5'-O-dimethoxytrityl-2'-deoxyadenosine-3'-O-(2-cyanoethyl)-N,N-diisopropylphosphoramidite A 250 ml three-necked flask equipped with a magnetic stirrer, a gas inlet for argon, and a septum was assembled under an atmosphere of argon. All the glassware was dried at 120° C. for 1 hour. N6-Benzoyl-5'-O-DMT-2'-deoxyadenosine (3.7 mmole), pyridine (5.55 mmol) and acetonitrile (95 ml) were added to the flask followed by bis(diisopropylamino)chlorophosphine (4.44 mmol) at room temperature. The reaction mixture was stirred, and then a solution of 3-hydroxypropionitrile (4.28 mmol) in acetonitrile (5 ml) dried over 4 A molecular sieves was added. The reaction mixture was stirred at room temperature for 12 hour. All the volatiles were removed under reduced pressure and the residue extracted into an organic solvent, washed with aqueous sodium bicarbonate solution and dried. Concentration of the dried extract and purification using flash chromatography afforded the phosphoramidite as a colorless solid.

Example 15

N6-Benzoyl-5'-O-dimethoxytrityl-2'-deoxyadenosine-3'-O-(2-diphenylmethylsilylethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N6-Benzoyl-5'-O-DMT-2'-deoxyadenosine (3.7 mmole), pyridine (5.55 mmol) and acetonitrile (95 ml) are added to the flask followed by bis(diisopropylamino) chlorophosphine (4.44 mole) at room temperature. The reaction mixture is stirred for 20 minutes and a solution of 2-diphenylmethylsilylethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

Example 16

N6-Benzoyl-5'-O-dimethoxytrityl-2'-deoxyadenosine-3'-O-(N-methyl-N-trifluoroacetylaminoethyl)-N,N-diisopropylphosphoramidite A 250 ml three-necked flask equipped with a magnetic stirrer, a gas inlet for argon, and a septum is assembled under an atmosphere of argon. All the glassware is dried at 120° C. for 1 hour. N6-Benzoyl-5'-O-DMT-2'-deoxyadenosine (3.7 mmole), pyridine (5.55 mmol) and acetonitrile (95 ml) are added to the flask followed by bis(diisopropylamino) chlorophosphine (4.44 mmol) at room temperature. The reaction mixture is stirred for 20 minutes and a solution of N-methyl-N-trifluoroacetylethyl alcohol (4.28 mmol) in acetonitrile (5 ml) dried over 4 A molecular sieves is added. The reaction mixture is stirred at room temperature for 12 hours. All the volatiles are removed under reduced pressure and the residue extracted into an organic solvent, washed with aqueous sodium bicarbonate solution and dried. Concentration of the dried extract and purification using flash chromatography affords the phosphoramidite as a colorless solid.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the preparation of a phosphoramidite having the Formula:

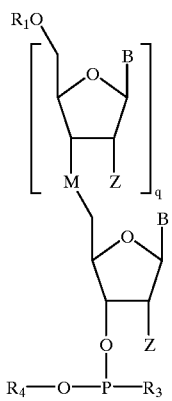

wherein:

$R_1$ is a hydroxyl protecting group;

B is a nucleobase;

M is an internucleotide linkage;

q is 1 to about 100;

Z is H, OH, F, or a group of formula $R_7$—$(R_8)_n$;

$R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;

$R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

n is from 0 to about 10;

$R_3$ is a group of formula —$N(R_5)(R_6)$;

$R_5$ and $R_6$ are independently alkyl having from one to four carbon atoms, or $R_5$ and $R_6$ taken together with the nitrogen atom to which they are attached form an aliphatic or aromatic five or six membered ring;

$R_4$ is a phosphorous protecting group; comprising:

providing a solution consisting of a compound of Formula I:

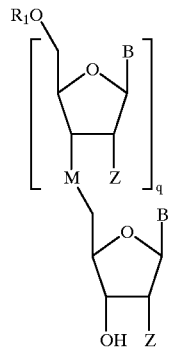

in a solvent;

reacting the compound of Formula I in the solvent with a diaminohalophosphine of Formula:

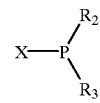

wherein X is halogen; and $R_2$ is a group of formula —$N(R_5)(R_6)$ to produce a reaction mixture containing a phosphordiamidite of Formula II:

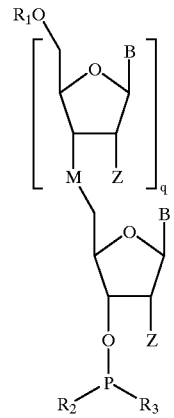

wherein the constituent variables are as defined previously; and contacting the reaction mixture containing the compound of Formula II with a reagent of Formula $R_4$—OH to produce the phosphoramidite.

2. The method of claim 1 wherein $R_1$ is trityl, monomethoxy trityl, dimethoxytrityl, trimethoxytrityl, 2-chlorotrityl, DATE, TBTr, 9-phenylxanthine-9-yl (Pixyl) or 9-(p-methoxyphenyl)xanthine-9-yl (MOX).

3. The method of claim 1 wherein $R_1$ is trityl, monomethoxy trityl or dimethoxytrityl.

4. The method of claim 1 wherein each $R_5$ and $R_6$ are the same.

5. The method of claim 1 wherein $R_5$ and $R_6$ are each alkyl.

6. The method of claim 1 wherein each $R_5$ and $R_6$ is isopropyl.

7. The method of claim 1 wherein Z is H, OH, F, or a group of formula $R_7$—$(R_8)_n$ where $R_7$ is $C_1$–$C_{20}$ alkoxy, $C_2$–$C_{20}$ alkenyloxy, or $C_2$–$C_{20}$ alkynyloxy; $R_8$ is hydrogen; and n is 1.

8. The method of claim 1 wherein $R_4$ is β-cyanoethyl, diphenylsilylethyl, δ-cyanobutenyl, cyano p-xylyl (CPX), N-methyl-N-trifluoroacetyl ethyl (META), acetoxyphenoxyethyl, or butene-4-yl.

9. The method of claim 1 wherein $R_4$ is β-cyanoethyl, diphenylsilylethyl, δ-cyanobutenyl, acetoxyphenoxyethyl or cyano p-xylyl.

10. The method of claim 1 wherein X is chlorine.

11. The method of claim 7 wherein $R_4$ is β-cyanoethyl, diphenylsilylethyl, δ-cyanobutenyl, acetoxy phenoxy ethyl or cyano p-xylyl; and each $R_5$ and $R_6$ is alkyl.

12. The method of claim 11 wherein each $R_5$ and $R_6$ is isopropyl.

13. The method of claim 1 wherein said solvent is acetonitrile or dichloromethane.

14. The method of claim 13 wherein said solvent is acetonitrile.

15. The method of claim 13 wherein the nucleoside is reacted with the diaminohalophosphine in the presence of a base.

16. The method of claim 15 wherein said base is Hunig's base, pyridine, triethylamine or a mixture of pyridine and triethylamine.

17. The method of claim 1 wherein the nucleoside phosphordiamidite is contacted with the reagent of formula $R_4$—OH in the presence of triethylamine, pyridine or a mixture thereof.

18. A method for the preparation of a mononucleoside phosphoramidite in a single pot reaction sequence comprising the steps of:
    reacting a mononucleoside having a free 3'-hydroxyl with a diaminohalophosphine in a solvent thereby forming a reaction mixture; and
    contacting said reaction mixture with a reagent of formula $R_4$—OH, where $R_4$ is a phosphorus protecting group, under conditions of time and temperature sufficient to form the mononucleoside phosphoramidite.

19. A method for the preparation of a phosphoramidite in a single pot reaction sequence, said phosphoramidite having the Formula:

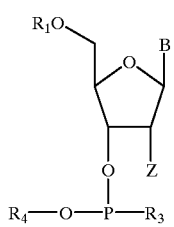

wherein:
$R_1$ is a hydroxyl protecting group;
B is a nucleobase;
Z is H, OH, F, or a group of formula $R_7$—$(R_8)_n$;
$R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;
$R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
n is from 0 to about 10;
$R_3$ is a group of formula —$N(R_5)(R_6)$;
$R_5$ and $R_6$ are independently alkyl having from one to four carbon atoms, or $R_5$ and $R_6$ taken together with the nitrogen atom to which they are attached form an aliphatic or aromatic five or six membered ring;
$R_4$ is a phosphorus protecting group; comprising:
    providing a solution consisting of a compound of Formula III:

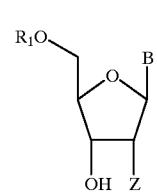

in a solvent;
reacting the compound of Formula III in the solvent with a diaminohalophosphine of Formula:

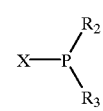

wherein X is halogen; and $R_2$ is a group of formula —$N(R_5)(R_6)$; to produce a reaction mixture containing a phosphordiamidite of Formula IV:

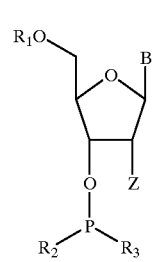

wherein the constituent variables are as defined previously; and
contacting the reaction mixture containing the compound of Formula IV with a reagent of Formula $R_4$—OH to produce the nucleoside phosphoramidite.

20. A method for the preparation of an oligonucleotide phosphoramidite in a single pot reaction sequence comprising the steps of:
    reacting an oligonucleotide having a free 3'-hydroxyl with a diaminohalophosphine in a solvent thereby forming a reaction mixture; and
    contacting said reaction mixture with a reagent of formula $R_4$—OH, where $R_4$ is a phosphorus protecting group, under conditions of time and temperature sufficient to form the oligonucleotide phosphoramidite.

21. The method of claim 19 wherein $R_1$ is trityl, monomethoxy trityl, dimethoxytrityl, trimethoxytrityl, 2-chlorotrityl, DATE, TBTr, 9-phenylxanthine-9-yl (Pixyl) or 9-(p-methoxyphenyl)xanthine-9-yl (MOX).

22. The method of claim 19 wherein $R_1$ is trityl, monomethoxy trityl or dimethoxytrityl.

23. The method of claim 19 wherein each $R_5$ and $R_6$ are the same.

24. The method of claim 19 wherein $R_5$ and $R_6$ are each alkyl.

25. The method of claim 19 wherein each $R_5$ and $R_6$ is isopropyl.

26. The method of claim 19 wherein Z is H, OH, F, or a group of formula $R_7$—$(R_8)_n$ where $R_7$ is $C_1$–$C_{20}$ alkoxy, $C_2$–$C_{20}$ alkenyloxy, or $C_2$–$C_{20}$ alkynyloxy; $R_8$ is hydrogen; and n is 1.

27. The method of claim 19 wherein $R_4$ is β-cyanoethyl, diphenylsilylethyl, δ-cyanobutenyl, cyano p-xylyl (CPX), N-methyl-N-trifluoroacetyl ethyl (META), acetoxy phenoxy ethyl, or butene-4-yl.

28. The method of claim 19 wherein $R_4$ is β-cyanoethyl, diphenylsilylethyl, δ-cyanobutenyl, acetoxy phenoxy ethyl or cyano p-xylyl.

29. The method of claim 19 wherein X is chlorine.

30. The method of claim 26 wherein $R_4$ is β-cyanoethyl, diphenylsilylethyl, δ-cyanobutenyl, acetoxy phenoxy ethyl or cyano p-xylyl; and each $R_5$ and $R_6$ is alkyl.

31. The method of claim 30 wherein each $R_5$ and $R_6$ is isopropyl.

32. The method of claim 19 wherein said solvent is acetonitrile or dichloromethane.

33. The method of claim 32 wherein said solvent is acetonitrile.

34. The method of claim 32 wherein the nucleoside is reacted with the diaminohalophosphine in the presence of a base.

35. The method of claim 34 wherein said base is Hunig's base, pyridine, triethylamine or a mixture of pyridine and triethylamine.

36. The method of claim 19 wherein the nucleoside phosphordiamidite is contacted with the reagent of formula $R_4$—OH in the presence of triethylamine, pyridine or a mixture thereof.

* * * * *